United States Patent
Sarkar et al.

(10) Patent No.: US 10,228,313 B2
(45) Date of Patent: Mar. 12, 2019

(54) SYSTEM AND METHOD FOR MULTIPLEXED AFFINITY PURIFICATION OF PROTEINS AND CELLS

(71) Applicants: Massachusetts Institute of Technology, Cambridge, MA (US); The Massachusetts General Hospital, Boston, MA (US)

(72) Inventors: Aniruddh Sarkar, Cambridge, MA (US); Han Wei Hou, Singapore (SG); Jongyoon Han, Bedford, MA (US); Galit Alter, Winchester, MA (US)

(73) Assignees: Massachusetts Institute of Technology, Cambridge, MA (US); The Massachusetts General Hospital, Boston, MA (US)

(*) Notice: Subject to any disclaimer, the term of this patent is extended or adjusted under 35 U.S.C. 154(b) by 0 days.

(21) Appl. No.: 15/520,176

(22) PCT Filed: Oct. 23, 2015

(86) PCT No.: PCT/US2015/057146
§ 371 (c)(1),
(2) Date: Apr. 19, 2017

(87) PCT Pub. No.: WO2016/077055
PCT Pub. Date: May 19, 2016

(65) Prior Publication Data
US 2017/0307488 A1  Oct. 26, 2017

Related U.S. Application Data

(60) Provisional application No. 62/068,431, filed on Oct. 24, 2014.

(51) Int. Cl.
*G01N 1/40* (2006.01)
*C12Q 1/24* (2006.01)
*B01L 3/00* (2006.01)

(52) U.S. Cl.
CPC ........ *G01N 1/405* (2013.01); *B01L 3/502707* (2013.01); *B01L 3/502761* (2013.01); *B01L 3/502776* (2013.01); *C12Q 1/24* (2013.01); *B01L 2200/0652* (2013.01); *B01L 2300/088* (2013.01); *B01L 2300/0816* (2013.01); *B01L 2300/0864* (2013.01); *B01L 2400/0409* (2013.01); *B01L 2400/0487* (2013.01)

(58) Field of Classification Search
CPC ................................................ B01L 3/502707
See application file for complete search history.

(56) References Cited

U.S. PATENT DOCUMENTS

| | | |
|---|---|---|
| 2013/0016335 A1 | 1/2013 | Lo et al. |
| 2013/0130226 A1 | 5/2013 | Lim et al. |
| 2013/0209988 A1 | 8/2013 | Barber et al. |

FOREIGN PATENT DOCUMENTS

| | | |
|---|---|---|
| WO | WO 2013/085797 A1 | 6/2013 |
| WO | WO 2014/152643 A2 | 9/2014 |
| WO | WO 2016/077055 A1 | 5/2016 |

OTHER PUBLICATIONS

Kuntaegowdanahalli et al., Lab Chip, 2009, 9:2973-2980.*
Ozkumur et al. Sci Transl Med., 2013, 5(179): pp. 1-20 as printout.*
International Search Report and Written Opinion of the International Searching Authority for International Application No. PCT/US2015/057146, entitled "System and Method for Multiplexed Affinity Purification of Proteins and Cells", dated Apr. 21, 2016.
International Preliminary Report on Patentability for International Application No. PCT/US2015/057146, entitled "System and Method for Multiplexed Affinity Purification of Proteins and Cells", dated Apr. 25, 2017.
A. Sarkar, et al., "Inertial Microfluidics for Multiplexed Affinity Separation of Proteins and Cells", 18th International Conference on Miniaturized Systems for Chemistry and Life Sciences, Oct. 26, 2014, pp. 246-248.
Kodituwakku, et al., "Isolation of antigen-specific B cells", Immunology and Cell Biology vol. 81, pp. 163-170 (2003).
Pape, et al., "Different B cell populations mediate early and late memory during an endogenous immune response", Science 331, 1203-1207 (2011). doi:10.1126/science.1201730.
Bhagat, et al., "Continuous particle separation in spiral microchannels using Dean flow based differential migration", Lab Chip 8, 1906-1914 (2008).
Hou, et al., "Isolation and retrieval of circulating tumor cells using centrifugal forces", Sci. Rep. 3, 1259, pp. 1-8 (2013). http://www.nature.com/srep/2013/130212/srep01259/abs/srep01259.html-supplementary-information.
Ozkumur, et al., "Inertial Focusing for Tumor Antigen-Dependent and Independent Sorting of Rare Circulating Tumor Cells", Sci Trans Med, 5(179): 179, 179ra47 (2013).

* cited by examiner

*Primary Examiner* — Bin Shen
(74) *Attorney, Agent, or Firm* — Hamilton, Brook, Smith & Reynolds, P.C.

(57) ABSTRACT

In accordance with an embodiment of the invention, there is provided a method for: a) high-throughput, multiplexed, affinity-based separation of proteins—especially low abundance proteins—from complex biological mixtures such as serum; and b) high-throughput, multiplexed, affinity-based separation of cells—especially rare cells—from complex biological mixtures such as blood or blood fractions. The separation of proteins or cells is achieved based on differential binding to affinity-capture beads of different sizes and then sorting the protein-bound or cell-bound beads using the concept of centrifugal-induced Dean migration in a spiral microfluidic device. This method enables continuous-flow, high throughput affinity-separation of milligram-scale protein samples or millions of cells in minutes after binding. This is particularly applicable to the isolation of antigen-specific antibodies from polyclonal sera and antigen-specific immune cells or circulating tumor cells from blood, both of which are otherwise highly labor-intensive and expensive to perform.

11 Claims, 10 Drawing Sheets

SYSTEM AND METHOD FOR MULTIPLEXED AFFINITY PURIFICATION OF PROTEINS AND CELLS

RELATED APPLICATION

This application is the U.S. National Stage of International Application No. PCT/US2015/057146, filed Oct. 23, 2015, which designates the U.S., published in English, and claims the benefit of U.S. Provisional Application No. 62/068,431, filed on Oct. 24, 2014. The entire teachings of the above applications are incorporated herein by reference.

GOVERNMENT SUPPORT

This invention was made with Government support under Grant No. N66001-11-1-4182 awarded by the Space and Naval Warfare Systems Center. The Government has certain rights in the invention.

BACKGROUND OF THE INVENTION

Isolation of specific proteins and cells from complex biological mixtures such as blood serves as the essential first step in analytical and preparative methods involved in a range of diagnostic, therapeutic and research applications. Differences in easily accessible physical properties such as size and density form the basis of quick, inexpensive separation methods such as electrophoretic separation of proteins or density gradient centrifugation of cells often used in isolating abundant targets. However, for a large class of low abundance target proteins and rare cells, such as antigen-specific antibodies or immune cells, binding affinity to the cognate antigen is their only distinguishing characteristic and forms the basis of current isolation methods for them.

Isolation of multiple antigen-specific antibodies is currently most commonly performed using serially performed binding, washing and elution steps with separate affinity matrices for each antigen. This is time intensive and can be can be prohibitively so for low abundance antibodies as it can take hours to capture sufficient amount of antibody in each binding step. Also each binding step involves unavoidable loss of sample, making these methods particularly difficult to apply to low availability clinical samples.

Antigen-specific cells are currently isolated using either capture on antigen-coated solid matrices, rosetting with antigen-coated red blood cells or magnetic particles followed by density gradient centrifugation or magnetic separation respectively, or by staining with fluorescent antigen and isolation by flow cytometric cell sorting (FACS) (1). The cost of instrumentation for first two methods can be relatively low but they need to be serially applied for each antigen of interest. Also since they usually work as batch processes with relatively small batches of cells, isolating rare populations maybe can be challenging with these methods. FACS based methods can sort multiple (up to six in commercial instruments) selected cell populations simultaneously. Also since flow cytometry works at the single-cell level it can be used to identify and isolate relatively rare cells as well and indeed has been used to isolate rare antigen-specific B cell populations (2). However, the instrument cost is high which makes the method inaccessible. Also serially evaluating the fluorescence of every single cell results in a throughput bottleneck and usually at most about 10,000 cells per second can be handled. For very rare populations (<0.1%), this results in a prohibitively large amount of time required to isolate a sufficient number of cells for downstream processing.

SUMMARY OF THE INVENTION

In accordance with an embodiment of the invention, there is provided a method for: a) high-throughput, multiplexed, affinity-based separation of proteins—especially low abundance proteins—from complex biological mixtures such as serum; and b) high-throughput, multiplexed, affinity-based separation of cells—especially rare cells—from complex biological mixtures such as blood or blood fractions. The separation of proteins or cells is achieved based on differential binding to affinity-capture beads of different sizes and then sorting the protein-bound or cell-bound beads using the concept of centrifugal-induced Dean migration in a spiral microfluidic device. This is particularly applicable to the isolation of antigen-specific antibodies from polyclonal sera and antigen-specific immune cells or circulating tumor cells from blood, both of which are otherwise highly labor-intensive and expensive to perform.

In accordance with an embodiment of the invention, there is provided a method of separating at least one of a protein and a cell from a biological mixture. The method comprises flowing a plurality of types of at least one of proteins and cells through at least one inlet of a spiral microfluidic device, each different type of the at least one of proteins and cells being bound to a corresponding different size of bead, the binding being based on an affinity between each such type of the at least one of proteins and cells and at least a portion of a surface of a bead to which each such type is bound. The plurality of types of the at least one of proteins and cells, bound to the corresponding different sizes of beads, are flowed from the at least one inlet through a spiral channel of the spiral microfluidic device, thereby sorting, along a cross-section of the spiral channel, the plurality of types of the at least one of proteins and cells based on effective sizes of a plurality of combination particles, each combination particle comprising a type of the at least one of the protein and the cell bound to the corresponding different size of bead to which each type of the at least one of the protein and the cell is bound. The sorted types of the at least one of proteins and cells are flowed through a plurality of outlets of the spiral microfluidic device that are in fluid flow connection with the spiral channel, such that each outlet flows substantially only one type of the at least one of proteins and cells, bound to the corresponding different size of bead to which each such type is bound.

In another embodiment according to the invention, there is provided a microfluidic system for separating at least one of a protein and a cell from a biological mixture. The system comprises at least one inlet of a spiral microfluidic device, the at least one inlet being configured to receive a plurality of types of at least one of proteins and cells, each different type of the at least one of proteins and cells being bound to a corresponding different size of bead, the binding being based on an affinity between each such type of the at least one of proteins and cells and at least a portion of a surface of a bead to which each such type is bound. The system further comprises a spiral channel of the spiral microfluidic device, in fluid flow connection with the at least one inlet, the spiral channel being adapted to flow the plurality of types of the at least one of proteins and cells, bound to the corresponding different sizes of beads, received from the at least one inlet, thereby sorting, along a cross-section of the spiral channel, the plurality of types of the at least one of proteins and cells based on effective sizes of a plurality of combination particles, each combination particle comprising a type of the at least one of the protein and the cell bound to the corresponding different size of bead to which each type of the at least one of the protein and the cell is bound. Further, the system comprises a plurality of outlets of the spiral microfluidic device in fluid flow connection with the spiral channel, the plurality of outlets being configured to flow the sorted types of the at least one of proteins and cells such that each outlet flows substantially only one type of the at least one of proteins and cells, bound to the corresponding different size of bead to which each such type is bound.

In further, related method and system embodiments, the at least one of the protein and the cell may comprise an antigen-specific antibody. The at least one of the protein and the cell may comprise an antigen-specific cell. The at least one of the protein and the cell may comprise a circulating tumor cell. The biological mixture may comprise at least one blood component. The biological mixture may comprise whole blood. The biological mixture may comprise serum, such as a polyclonal serum. Each size bead of the corresponding different sizes of beads may comprise a coated surface comprising a different type of at least one of an antigen or antibody that comprises an affinity with the corresponding at least one of the protein and the cell. The plurality of types of at least one of proteins and cells may comprise more than two types of at least one of proteins and cells. The spiral channel may have a length, and the cross-section may have a height and a width defining an aspect ratio, such that the spiral channel is adapted, by virtue of the length and the cross-section, to sort, along a cross-section of the spiral channel, the plurality of types of the at least one of proteins and cells based on the effective sizes of the plurality of combination particles.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 2A is a diagram of a fabricated PDMS-glass spiral microchannel. FIG. 2B is a diagram of focused particle streams flow in separate device outlets designed to capture them. FIG. 2C is a set of sample flow cytometry plots of input mixture of beads and bead suspension collected from each outlet. FIG. 2D is a graph of locations of streams of particles of different diameters inside the DFF device. FIG. 2E is a bar graph of bead separation efficiency as measured by the concentration of each bead present at each outlet shown here normalized to its input concentration. FIG. 2F is a graph of fraction of capture of antigen-specific antibodies from samples after binding to a mixture of beads. FIG. 2G is a bar graph of normalized antigen binding titers of antibodies eluted from beads obtained at each outlet. FIG. 2H is a bar graph of multiplex isolation of two different antigen-specific antibodies. FIG. 2I is a bar graph of percentage loss of viability indicating dye (CFSE) for a population of gp120-coated target CEM cells that were incubated with the gp120-specific antibody isolated.

FIG. 3A is a schematic diagram illustrating that bead-cell pairs show similar focusing positions as that of single particles with the bigger of the two sizes or the sum of two sizes depending on if they are equal or unequal in size respectively. FIGS. 3B, 3C and 3D are bar graphs illustrating results for T cells (~6-8 μm in diameter) bound to 6 μm (FIG. 3B), 10 μm (see FIG. 3C) and 15 μm beads (see FIG. 3D) beads. FIG. 3E is a bar graph illustrating separation of T Cells (labeled with PE-anti-CD3) and B Cells (labeled with FITC-anti-CD19) from rest of PBMC by binding to 10 μm anti-PE coated bead and 15 μm anti-FITC coated beads at an optimized sample flow rate of 170 μL/min and sheath flow rate of 1750 μL/min. FIG. 3F is a bar graph illustrating separation of CD4+ and CD8+ cells from rest of PBMC by bead binding and flow rate. FIG. 3G is a bar graph of single-step isolation of CD4+ cells from whole blood. FIGS. 3H-I show isolation of rare gp120-specific B cells from PBMC from HIV-infector donors. FIGS. 3J-K show verification of antigen-specificity of secreted antibodies, of FIG. 3I, using a microengraving technique.

FIGS. 4A and 4B show the isolation of HIV p24-specific cells and gp41-specific cells (<1 in 10,000), respectively, from PBMC from HIV patients. FIG. 4C shows the isolation of tetanus-specific cells (<1 in 100,000) from PBMC from a healthy donor.

DETAILED DESCRIPTION OF THE INVENTION

Figure 1:
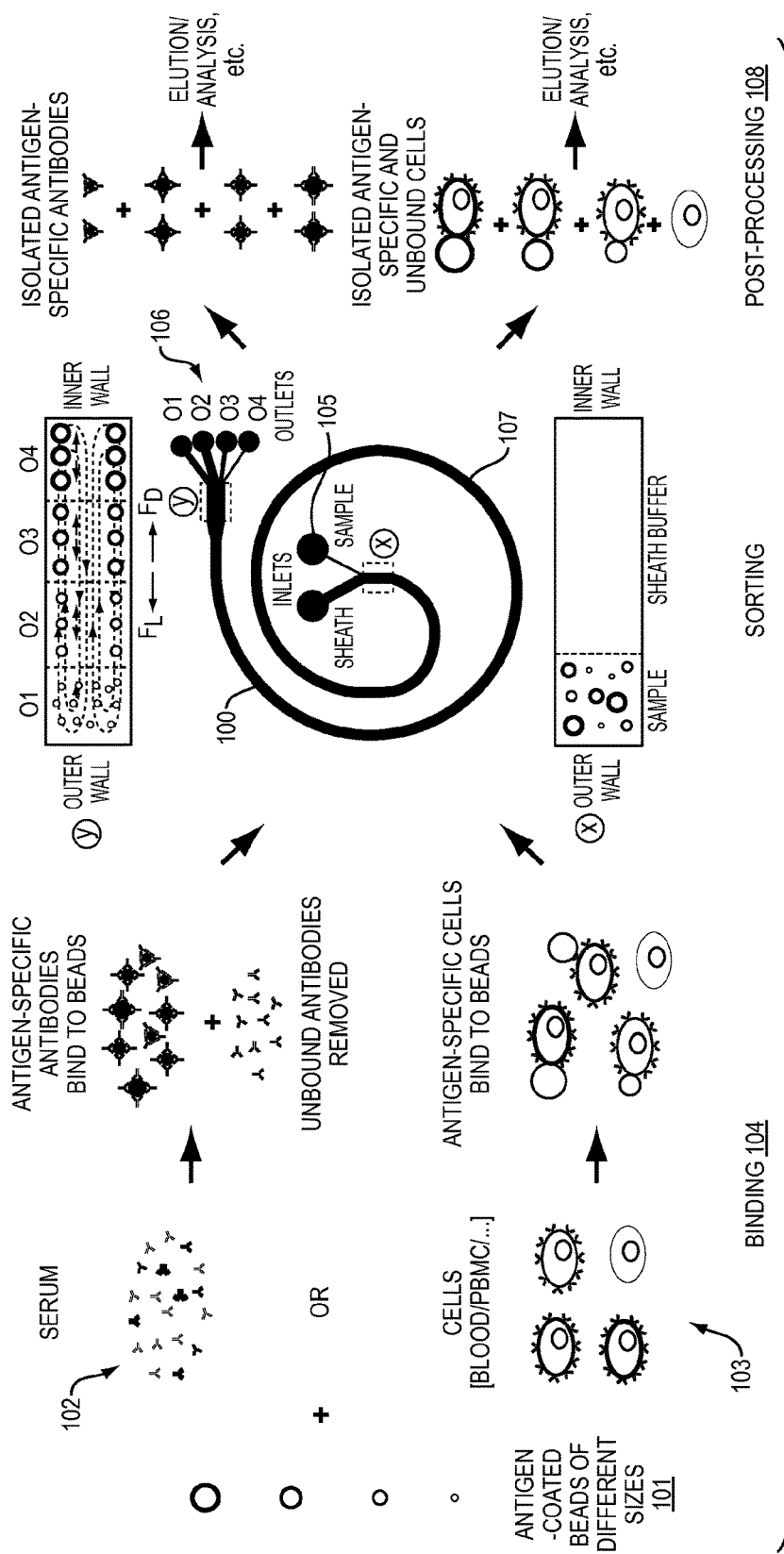
FIG. 1 is a schematic diagram illustrating a method of multiplexed antigen-specific antibody and cell sorting using a Dean Flow Fractionation (DFF) device, in accordance with an embodiment of the invention.

A description of example embodiments of the invention follows.

In accordance with an embodiment of the invention, there is provided a microfluidics-based technology platform that can be used for affinity-based separation of proteins and cells in a multiplexed and high throughput manner.

Isolation of low abundance proteins or rare cells from complex mixtures, such as blood, is required for many diagnostic, therapeutic and research applications. Current affinity-based protein or cell separation methods use binary 'bind-elute' separations and are inefficient when applied to the isolation of multiple low-abundance proteins or cell types. Embodiments of the present invention include a method for rapid and multiplexed, yet inexpensive, affinity-based isolation of both proteins and cells, using a size-coded mixture of multiple affinity-capture microbeads and an inertial microfluidic particle sorter device. For example, in a single binding step, different targets—cells or proteins—bind to beads of different sizes, which are then sorted by flowing them through a spiral microfluidic channel. Embodiments of the invention performs continuous-flow, high throughput affinity-separation of milligram-scale protein samples or millions of cells in minutes after binding. Additionally, embodiments can enable simultaneous isolation of multiple antibodies from serum and multiple cell types from peripheral blood mononuclear cells or whole blood. For example, to isolate low abundance antibodies specific to different HIV antigens and rare HIV-specific cells from blood obtained from HIV+ patients.

Embodiments of the invention include a simple, flexible and highly extensible, yet inexpensive scheme for high throughput, multiplexed affinity-based separation of both proteins and cells. Embodiments can provide sufficient throughput in a single device (104-107 beads per second) to support a number of downstream applications. For protein separation, milligram-scale amounts could be processed and for cell separation, 1-5 million cells can be processed each in less than 10 minutes. Parallelizing multiple devices can further increase this throughput. Multiplexing beyond four bead sizes is also possible with optimization of device geometry, by cascading devices tuned to different bead size ranges or by sequentially using this device along with other separation mechanisms such as magnetic sorting.

The use of a microfluidic platform for affinity separation also enables integration of the present sample preparation technique as a module into a complete lab-on-chip system, which can offer inexpensive, sample-to-answer automation and standardization. For example, microfluidic antigen-specific antibody isolation can be used to reduce the cost of purification in the monoclonal antibody manufacturing pipeline where up to 80% of the total cost is related to purification only. Some embodiments can be integrated with other techniques for example: microfluidic enzymatic digestion of antibody glycans and microcapillary electrophoresis for glycan sequencing to develop an integrated antigen-specific antibody glycosylation analysis chip. Similarly, rapid isolation of antigen-specific B cells integrated with microfluidic single B cell sequencing and potentially antibody expression can enable rapid identification of novel antibodies which currently is a laborious process that requires specialized FACS machines to handle highly infectious samples. Especially in the context of emerging epidemics in resource-poor settings, where monoclonal therapeutics are needed rapidly, embodiments of the present invention can offer critically needed acceleration to the antibody discovery and development process. Overall, due to relative simplicity and robustness, embodiments of the present invention are useful both as a standalone sample preparation technique as well as for use in integrated lab-on-chip systems, both in the context of infectious diseases and beyond.

FIG. 1 is a schematic diagram illustrating a method of multiplexed antigen-specific antibody and cell sorting using a Dean Flow Fractionation (DFF) device 100, in accordance with an embodiment of the invention. Beads 101 of different sizes coated with different capture agents bind in a single step to the corresponding different antibodies 102 or cells 103 and are then sorted based on their size using the DFF device 100 after which they can be post-processed depending on downstream requirements. As shown in FIG. 1, this method involves a single binding step 104 in which the sample is incubated with a mixture of coated beads 101 of a number of different sizes each coated with a different capture agent (antigen or antibody). After binding, the mixture is flowed through at least one inlet 105 of the spiral microchannel device 100, which sorts all particles in the mixture into different outlets 106 based on their size. This device works on the principle of Dean Flow Fractionation (DFF) (3, 4). Particles above a certain size threshold when flowing through a spiral channel 107 ($d_p/h > 0.07$, where $d_p$ is the effective particle diameter and h is the channel height) can be focused into distinct streams due to the superposition of size-dependent inertial lift forces ($F_L$) and a drag force ($F_D$) due to the Dean flow generated as a result of centrifugal acceleration of the fluid, such as the counter-rotating fluid vortices it generates. The device 100 height, particle sizes and outlet positions can be designed to match a single outlet to each stream containing the different protein or cell-bound beads (Outlets 106, shown as O1-O4 in FIG. 1), which can thus be separated. Note that the specific device dimensions, namely channel height and number of outlets are designed for each application separately by experimental optimization. Specifically, two designs of (h=85 µm, n=4) and (h=115 µm, n=5) were used for antibody and cell separation, respectively, as shown in the following figures, while the radius and length of the spiral are as described in earlier work (6), the teachings of which, inducing including teachings regarding radius and length, are incorporated by reference in their entirety. All particles below the focusing threshold remain entrained in the Dean flow and can also be collectively guided into a separate outlet (outlet O4 of outlets 106 in FIG. 1). The output streams of particles are collected and used for downstream processing 108 of the bound cells or antibodies either with or without elution from the beads.

A technique in accordance with an embodiment of the invention is applicable to the multiplexed affinity-based isolation of proteins from any complex protein mixture and hence can, for example, be useful for developing proteomic sample preparation devices and kits. This technique is particularly attractive for the multiplexed separation of antibodies based on their antigen-specificity or by their subclass or type or subtype.

A technique in accordance with an embodiment of the invention is further applicable to the multiplexed affinity-based sorting of cells from any complex cell mixture and hence can be used, for example, for developing cell sorting and isolation devices, kits and instruments.

Magnetic bead based cell isolation kits currently work in a non-multiplexed manner and isolate one cell type at a time. Flow cytometry based cell sorters perform multiplexed cell sorting but are based on highly expensive instruments, which can sort only up to 10,000 cells per second. In accordance with an embodiment of the present invention, the complete cell sorting setup can be assembled inexpensively while very high multiplexed cell sorting speeds (>$10^6$ cells/second) are achievable. This technique is particularly attractive for the multiplexed separation of B cells or T cells based on their antigen-specificity. This can significantly enhance the throughput and drive down the cost of cell sorting in current antibody sequencing and antibody discovery platforms.

Further, the capability for isolation of cells directly from whole blood makes a device in accordance with an embodiment of the invention useful as an inline sample-processing module for many blood-processing diagnostic and research instruments, which currently depend on input of pre-isolated cells, which leads to higher effort and reduces repeatability of results depending on quality of input. For example, CD4 cell count needs to be regularly monitored for HIV+ individuals undergoing therapy. A device in accordance with an embodiment of the invention provides single-step isolation of CD4+ cells from whole blood, and so can be the sample preparation module for point-of-care CD4 cell counters.

Further, isolation of rare cancer cells or circulating tumor cells (CTCs) from blood independently represents a promising field for cancer diagnostics and research. Current affinity-based CTC isolation methods either operate in a batch mode, by binding a fixed volume of blood with magnetic beads, which leads to low yield of CTCs, or use continuous flow microfluidic platforms (4), which need complex and expensive multi-step separation principles. By contrast, a device in accordance with an embodiment of the invention performs affinity isolation in a single step from whole blood and hence can be much more robust and inexpensive.

As used herein, a "combination particle" can comprise a bound bead-cell pair or bound bead-protein pair, and an "effective size" is the size of such a combination particle that determines the focusing position of the combination particles at the outlets of the device, in accordance with teachings discussed below relative to FIGS. 3A-3F.

As used herein, to say that an outlet flows "substantially only" one type of proteins or cells means that a normalized measure of proteins or cells at the outlet finds that greater than about 70%, such as greater than about 80%, such as greater than about 90% of the proteins or cells at the outlet are of the one type of proteins or cells. For example, in FIG. 2G, below, it is taught that normalized antigen binding titers of antibodies eluted from beads are obtained at each outlet. Pure antibodies specific to each antigen are obtained at the respective outlet to which the beads coated with that antigen were directed, by which it is meant that a percentage of total eluted antibody (see FIG. 2G) is greater than about 70%, and as close as possible to 100%, for each outlet to which the respective beads are directed (see p24 outlet, gp41 outlet and gp120 outlet in FIG. 2G).

As will be appreciated by those of ordinary skill in the art, the microfluidic channel can have a variety of shapes (e.g., curved, spiral, multiloop, s-shaped, linear) provided that the dimensions of the channel are adapted to sort, along a cross-section of the channel, the different types of proteins or cells based on effective sizes of the protein/cell bound to bead.

In one embodiment, the height of the spiral channel can be in a range of between about 10 μm and about 200 μm, such as about 50 μm and about 140 μm. The width of the spiral channel can be in a range of between about 100 μm and about 700 μm. The length of the spiral channel can be in a range of between about 1 cm and about 10 cm, or more.

In one embodiment, the spiral channel can be a bi-loop spiral channel. In another embodiment, the spiral channel can be 2-loop spiral channel. In yet another embodiment, the spiral channel can be 3-loop spiral channel. In still another embodiment, the spiral channel can be 4-loop spiral channel. In another embodiment, the spiral channel can be 5-loop spiral channel, etc.

The radius of the spiral channel can be adapted to yield a Dean number in a range of between about 1 and about 10, such as a radius of about 1 cm that yields a Dean number equal to about 5. The length of the spiral channel can be equal to or greater than about 3 cm, such as about 9 cm, about 10 cm, about 15 cm, and about 20 cm. The width of the spiral channel can be in a range of between about 100 μm and about 1,000 μm, such as about 200 μm, about 300 μm, about 400 μm, about 500 μm, about 600 μm, about 700 μm, about 800 μm, and about 900 μm. The height of the spiral channel can be in a range of between about m and about 200 μm, such as about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, and about 190 μm. The aspect ratio of the channel can be in a range of between about 0.1 and about 1, such as about 0.12, about 0.2, about 0.3, about 0.4, about 0.5, about 0.6, about 0.7, about 0.8, and about 0.9. It will be appreciated that other values of all of the foregoing may be used, consistent with teachings herein.

As used herein, an "aspect ratio" is the ratio of a channel's height divided by its width and provides the appropriate cross section of the channel to sort, along a cross-section of the channel, the different types of proteins or cells based on effective sizes of the protein/cell bound to bead.

In accordance with an embodiment of the invention, microchannels, including spiral microchannels, may be used that are taught in U.S. Patent App. Pub. No. 2013/0130226 A1 of Lim et al., the entire disclosure of which is incorporated herein by reference. For example, among other things, teachings of flow rates, widths, heights, aspect ratios and lengths and other conditions relating to hydrodynamic isolation of particles may be used.

EXPERIMENTAL

1. Antigen-Specific Antibody Isolation

Figure 2B:
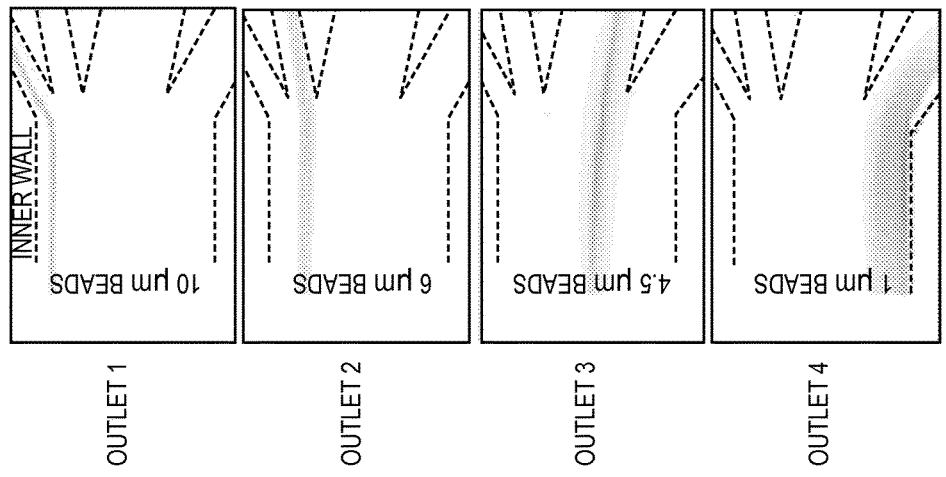
FIGS. 2A-2I are diagrams of a demonstration of multiplexed antigen-specific antibody isolation in an experiment in accordance with an embodiment of the invention.
Figure 2A:
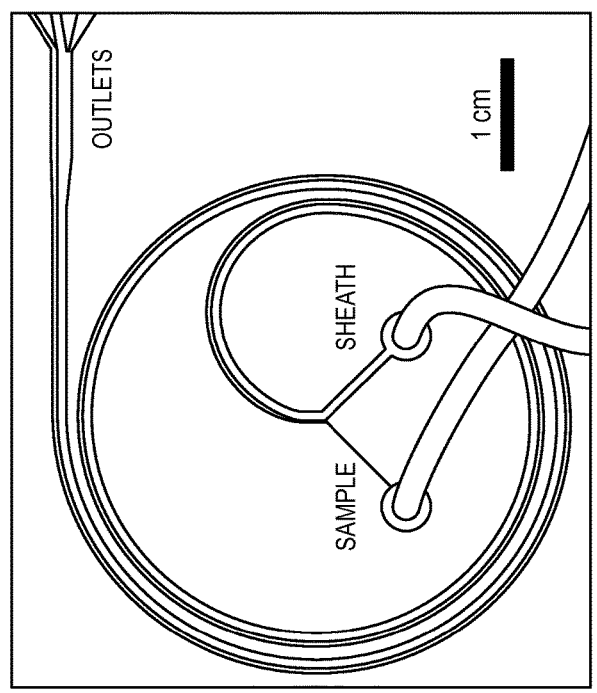
Figure 2C:
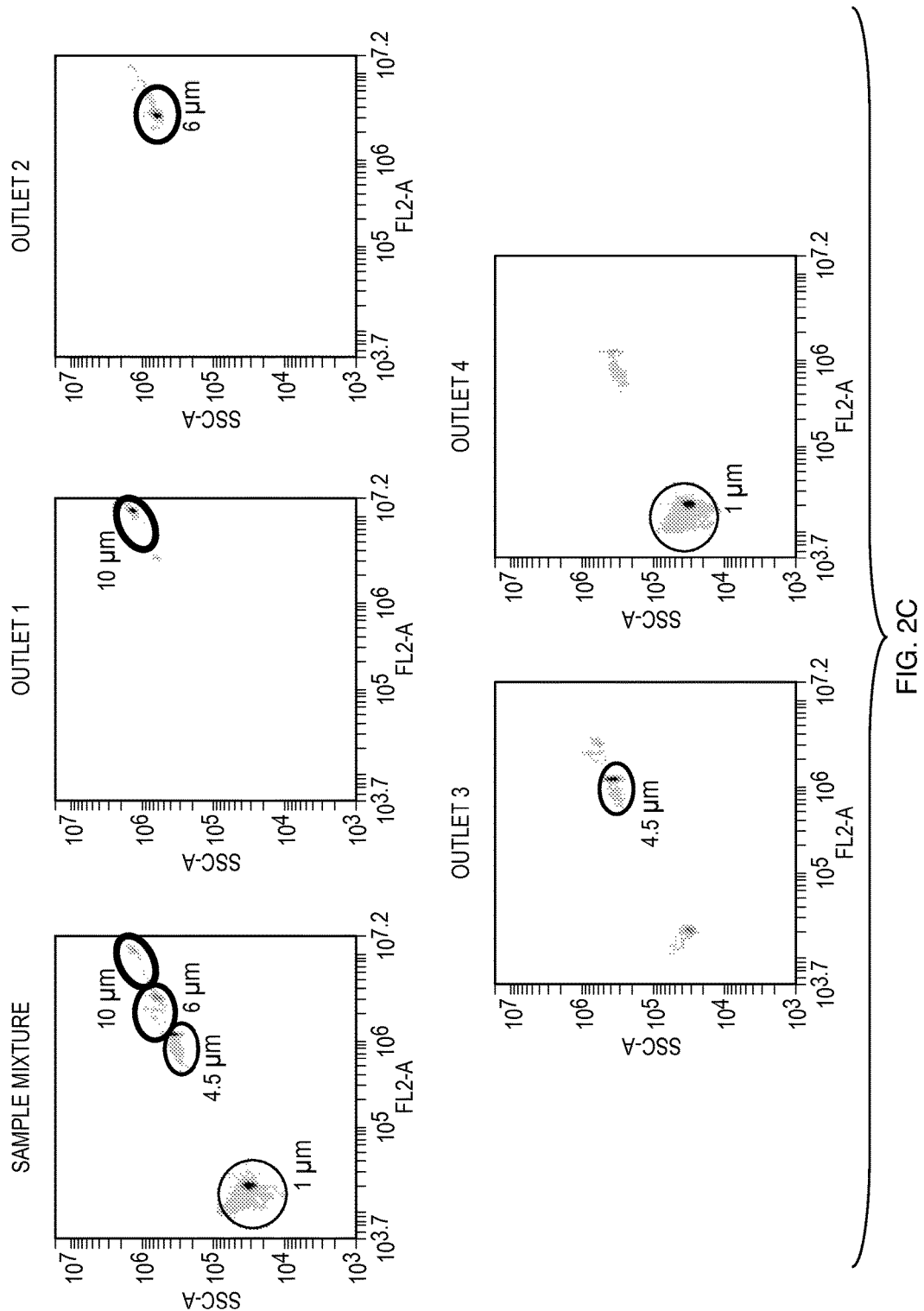
Figure 2D:
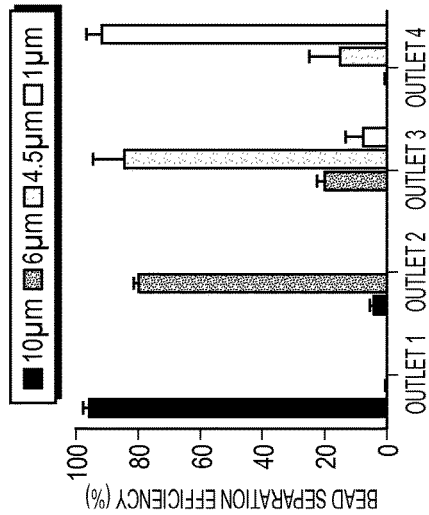
Figure 2E:
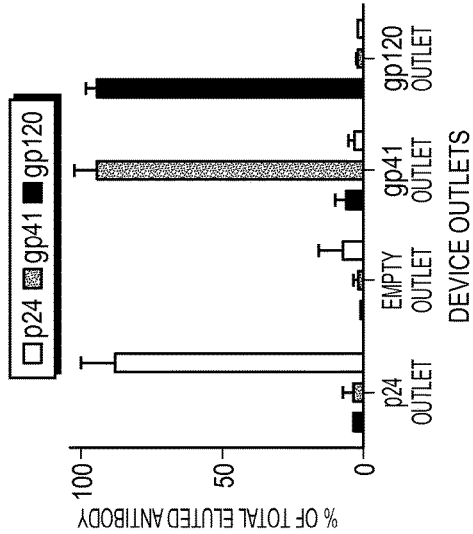
Figure 2F:
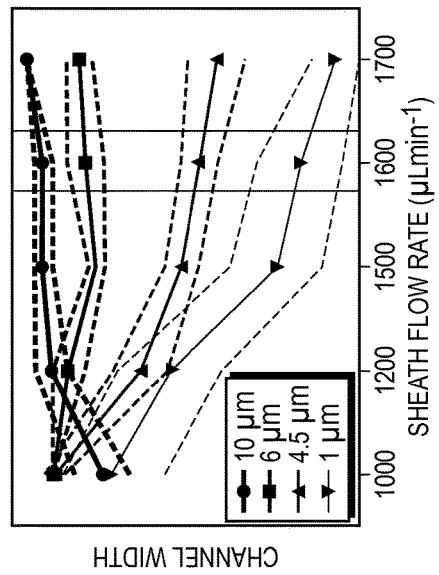
Figure 2G:
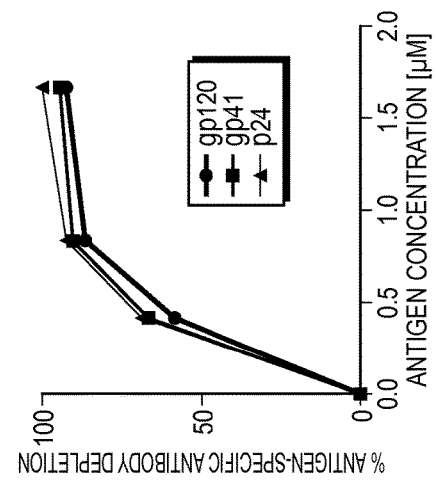

FIGS. 2A-2G are diagrams of a demonstration of multiplexed antigen-specific antibody isolation in an experiment in accordance with an embodiment of the invention. FIG. 2A is a diagram of a fabricated PDMS-glass spiral microchannel. FIG. 2B is a diagram of focused particle streams flow in separate device outlets designed to capture them. FIG. 2C is a set of sample flow cytometry plots of input mixture of beads and bead suspension collected from each outlet. FIG. 2D is a graph of locations of streams of particles of different diameters inside the DFF device. Different particle sizes focus into separate streams with separation depending on flow rate. Solid lines represent locations of the mean position of the particle stream and dotted lines represent its edges. An optimized flow rate from the highlighted range was chosen for further experiments. FIG. 2E is a bar graph of bead separation efficiency as measured by the concentration of each bead present at each outlet shown here normalized to its input concentration. Relative concentrations of beads were obtained using flow cytometry. FIG. 2F is a graph of fraction of capture of antigen-specific antibodies from samples after binding to a mixture of beads. Simultaneous depletion of antibodies against three different antigens is observed. FIG. 2G is a bar graph of normalized antigen binding titers of antibodies eluted from beads obtained at each outlet. Pure antibodies specific to each antigen are obtained at the respective outlet to which the beads coated with that antigen were directed.

In the experiments of FIGS. 2A-2G, a spiral microchannel device as described above was designed and fabricated (width, w=500 um, height, h=87 um) and mono-disperse suspensions of microparticles of various diameters were flowed through it to observe their focusing positions at different flow rates. Four particle sizes ($d_1$=10 μm, $d_2$=6 μm, $d_3$=4.5 μm, $d_4$=1 μm) were chosen which could be reliably directed into distinct streams at a range of flow rates. Outlets of the device were then designed to capture these separate streams. The focusing of the streams of particles of different sizes into these four outlets is shown in FIG. 2B. To verify particle separation, a mixed suspension of these particles was then flowed into the device and the fluid from each outlet was collected. The input and the outputs were analyzed by flow cytometry and the size purity of each outlet was verified (as shown in FIG. 2C). A sample set of flow cytometry plots is shown in FIG. 2C. Antigen-specific antibody separation was then performed using the device geometry and bead sizes found above. HIV antigens p24, gp41 and gp120 were coated on beads of different sizes via biotinylation and binding to streptavidin covalently linked to the bead surface. In a single binding step, mixtures of coated and washed beads were incubated with samples, which consisted of Immunoglobulin G (IgG) fraction of sera from HIV-infected patients. Magnetic or non-magnetic polystyrene beads were used with equivalent efficacy and the bead mixture was pelleted using a magnet or by centrifugation and the depleted supernatant was collected.

Specific antigen-binding titers of the depleted sample were measured after this binding step using Enzyme Linked Immunosorbent Assays (ELISA). Simultaneous depletion of all three antigen-binding titers dependent on the effective antigen concentration was observed (as shown in FIG. 2F). The antibody-bound beads were sorted using the device and antibodies were eluted from each the bead suspension obtained at each of the outlets. An ELISA on these antibody suspensions verified the purity of the separated p24, gp41 and gp120 specific antibodies obtained (as shown in FIG. 2G). Only minimal cross-contamination (<5%) was observed.

The amount of HIV-specific antibodies in serum is known to vary between patients and can be around 0.5-1% of total IgG. A 1-5 μg amount of each antigen-specific antibody isolated from 1 mg of IgG using this technique. Overall, the milligram amount of input sample was processed using the device to isolate microgram amounts of target antigen-specific antibodies in less than 10 minutes after binding. This represents a more than 1000-fold improvement in microfluidic affinity separation throughput compared to earlier work 17. Compared to the traditional macro-scale antibody separation technique based on repeated bind-elute steps this technique, which required almost a full day to separate three different antibodies, this technique presents a 10-fold reduction in time required as well as significant reduction in manual labor required.

Figure 2H:
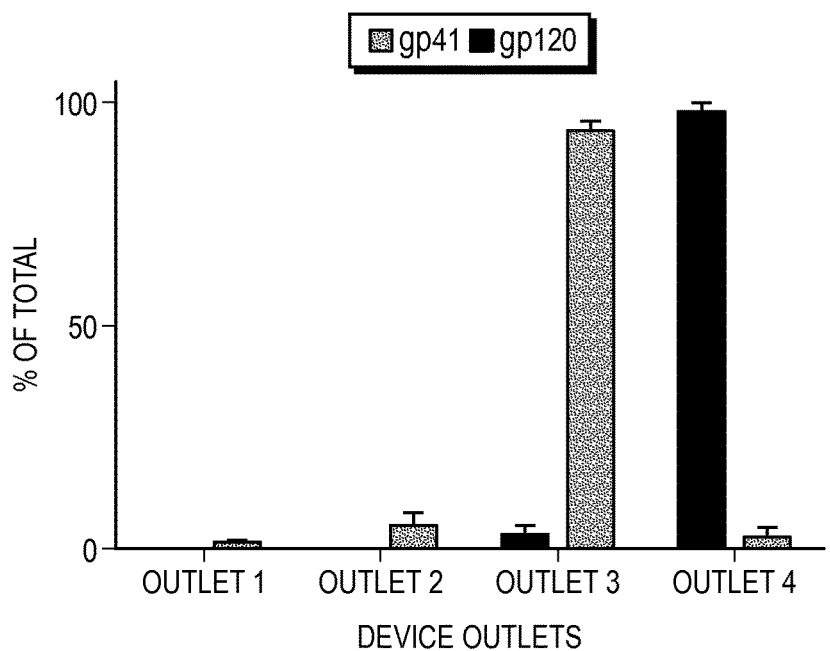

FIG. 2H is a bar graph of multiplexed isolation of two different antigen-specific antibodies. Normalized antigen binding titers of antibodies eluted from beads obtained at each outlet. Pure antibodies specific to each antigen are obtained at the respective outlet to which the beads coated with that antigen were directed. FIG. 2H shows similar results, as compared with FIG. 2G, were also obtained when isolating only two antigen-specificities.

Figure 2I:
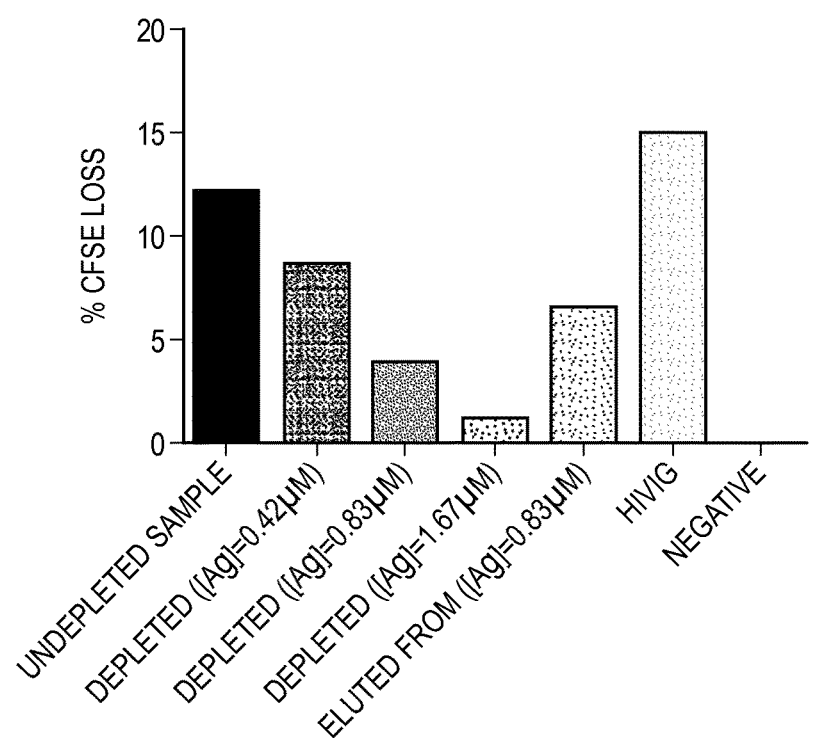

FIG. 2I is a bar graph of percentage loss of viability indicating dye (CFSE) from a population of gp120-coated target CEM cells in presence of a 10-fold excess of freshly isolated NK cells as effector cells and antibodies from various samples tested. An undepleted antibody sample from an HIV-infected subject shows cytotoxicity. Incubation of this sample with gp120-coated microbeads at increasing effective gp120 concentration causes decrease of this function. Antibodies eluted from these microbeads retain function. HIVIG and HIV negative IgG are used as positive and negative controls respectively. Specifically, Eluted gp120-specific antibodies were used in a functional assay for antibody-dependent cytotoxicity (ADCC). This assay creates an in-vitro model of antibody-induced lysis of virus-infected cells by recruiting natural killer (NK) immune cells. This involves both the antigen-binding (Fv) and the immune-activating (Fc) ends of antibody molecules. FIG. 2I shows that the antigen-specific antibodies were enriched intact and verified that this functional property could be interrogated after separation. The results of FIG. 2I further establishes the usefulness of the technique reported here as a multiplexed affinity-separation technique for antibodies which can be used for downstream functional assays.

2. Antigen-Specific Cell Isolation

In accordance with an embodiment of the invention, experiments analogous to those described above for antibody separation were performed to arrive at device geometry, set of particle sizes and flow rates suited for separation of cells. The separation of cells with different surface markers from freshly isolated human peripheral blood mononuclear cells (PBMC) was pursued in order to demonstrate the cell separation capability. Beads of different sizes coated with antibodies against different cell surface markers (for eg. CD3 and CD19) were used to bind and separate cells expressing those markers (T Cells and B Cells in this example) from PBMC which contain a mixture of a number of different kinds of cells.

Figure 3A:
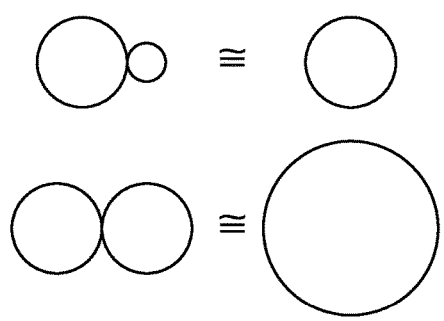
FIGS. 3A-3K are diagrams illustrating results of an experiment demonstrating multiplexed cell sorting in accordance with an embodiment of the invention.
Figure 3B:
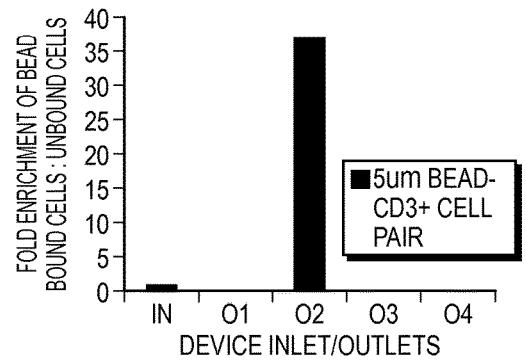
Figure 3C:
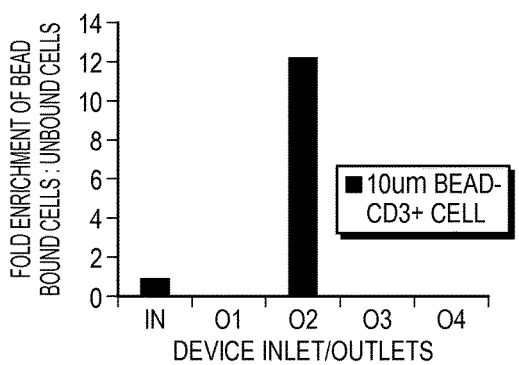
Figure 3D:
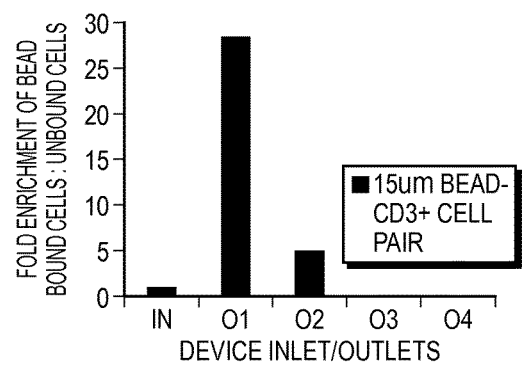
Figure 3E:
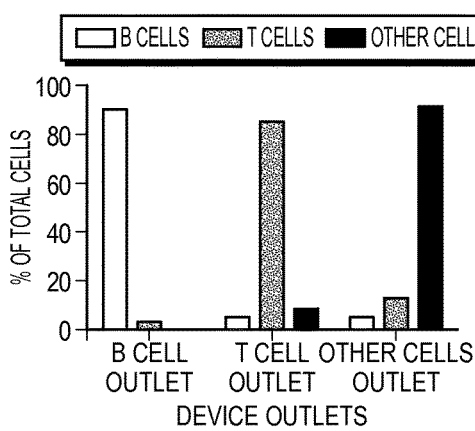
Figure 3F:
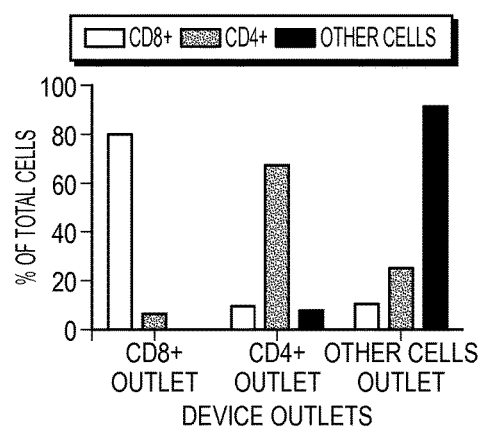

FIGS. 3A-3F are diagrams illustrating results of such an experiment, which demonstrate multiplexed cell sorting, in accordance with an embodiment of the invention. FIG. 3A is a schematic diagram illustrating that bead-cell pairs show similar focusing positions as that of single particles with the bigger of the two sizes or the sum of two sizes depending on if they are equal or unequal in size respectively. FIGS. 3B, 3C and 3D are bar graphs illustrating that T cells (~6-8 μm in diameter) bound to 6 μm (see FIG. 3B) or 100 μm (see FIG. 3C) beads are enriched into the same outlet, O2; but when bound to 15 μm beads (see FIG. 3D) are enriched to outlet O3. FIG. 3E is a bar graph illustrating separation of T Cells (labeled with PE-anti-CD3) and B Cells (labeled with FITC-anti-CD19) from rest of PBMC by binding to 10 μm anti-PE coated bead and 15 μm anti-FITC coated beads at an optimized sample flow rate of 170 μL/min and sheath flow rate of 1750 μL/min. FIG. 3F is a bar graph illustrating separation of CD4+ and CD8+ cells from rest of PBMC by bead binding and flow rate as optimized above.

It was observed that for bound bead-cell pairs where the bead and cell were of different sizes, the focusing position in the device, was set by the bigger of the two (i.e. $d_{pair}$~max $(d_p, d_{cell})$ if $d_{pair} \neq d_{cell}$) while if bead and cell were of equal sizes, they had an additive effect on the focusing position ($d_{eq}$~$d_p$+$d_{cell}$, if $d_p$~$d_{cell}$). This is depicted in schematic in FIG. 3A and demonstrated by the focusing and enrichment results shown in FIGS. 3B-3D. Here, T Cells bound to beads coated with an anti-CD3 antibody were focused into different outlets depending on the bead diameter. Without binding to beads, T cells (average diameter ~6-8 μm) focused into the outlet O3. The outlet O2, which nominally collects 10 μm beads was found to collect bead-cell pairs and no unbound cells, if either 6 μm ($d_p$~$d_{cell}$) or 10 μm beads ($d_p$>$d_{cell}$) were used for binding. The 15 μm outlet was found to collect bead-cell pairs only, if 15 μm beads ($d_p$>$d_{cell}$) were used for binding. Bead-cell pairs and unbound cells were found to flow into the same outlet (O3) if 2 μm or 4 μm beads were used for binding (data not shown).

Based on these results, an experiment was designed where 10 μm beads coated with an anti-Phycoerythrin (PE) antibody and 15 μm beads coated with an anti-fluorescein (FITC) antibody were incubated with PBMC stained with PE-labeled anti-CD3 and FITC-labeled anti-CD19 antibodies. This enabled sorting of T Cells and B Cells and other unbound cells into different outlets as shown in FIG. 3E. Similarly CD4+ and CD8+ T Cells could be sorted using beads coated with antibodies against those surface markers as shown in FIG. 3F.

Figure 3I:
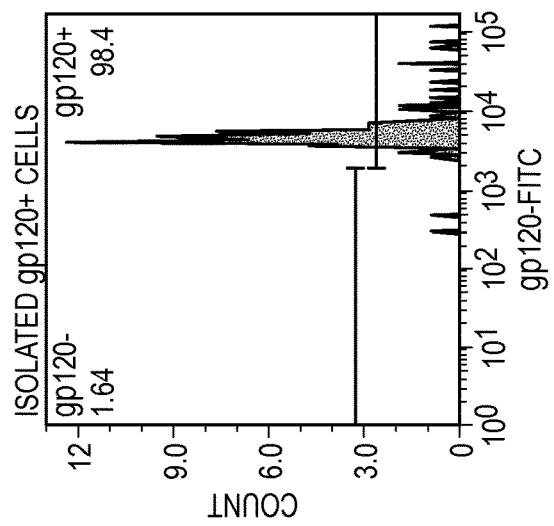
Figure 3H:
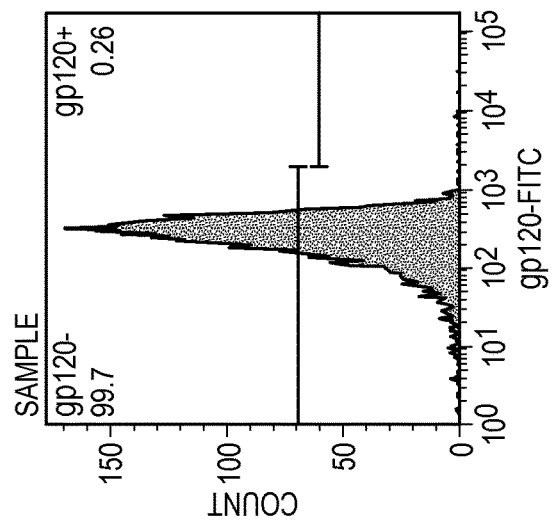
Figure 3G:
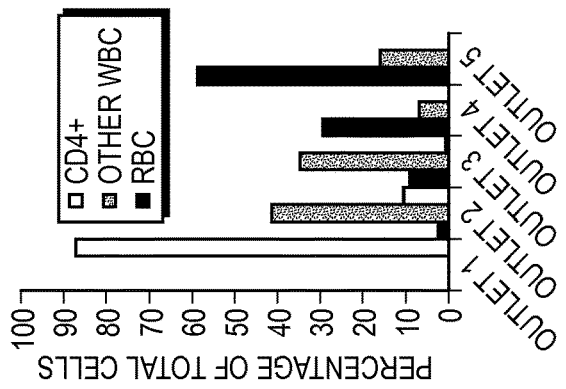

Direct isolation of specific cells from whole blood was also performed as shown in FIG. 3G, which shows the isolation of CD4+ cells, while directing other white blood cells (WBC) and red blood cells (RBC) to other outlets of the device.

Figure 3K:
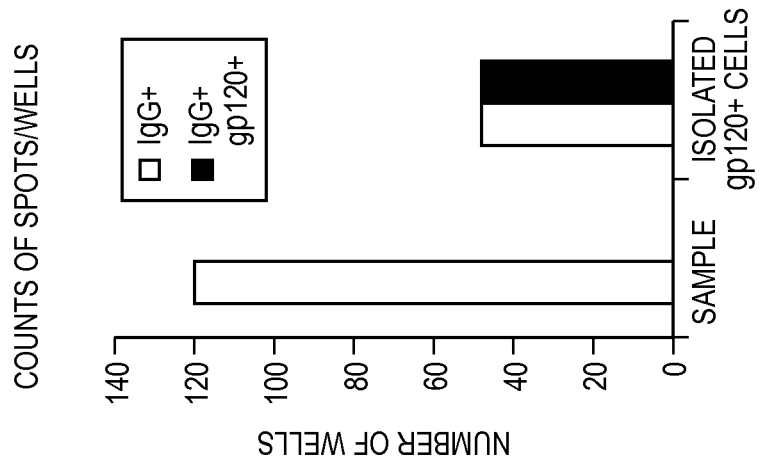
Figure 3J:
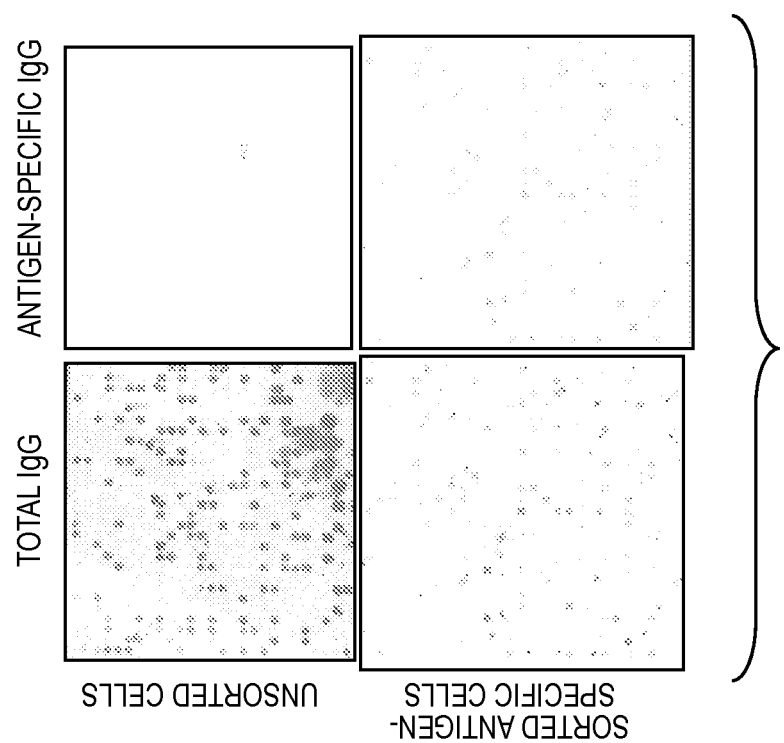

Isolation of rare antigen-specific cells could also be done by labeling them with fluorescent antigen tetramers and binding them with beads coated with antibodies against the fluorophore. FIG. 3I show the isolation of HIV gp120-specific B cells from PBMC from HIV patients. Only 0.26% of all B cells were gp120-specific, which amounts to only 0.025% of total cells in this sample (FIG. 3H). This rare fraction was isolated with >98% purity which represents a 4000-fold enrichment of the target cells. The isolated B cells were cultured and stimulating for antibody secretion. The antigen-specificity of secreted antibodies was then verified using a microengraving technique, as shown in FIGS. 3J-K, where antigen-specificity of antibodies secreted by single sorted cells was verified by microengraving after culturing the sorted cells and stimulating them to secrete antibodies. FIG. 3J shows fluorescence micrograph of capture slide after dual secondary labeling with FITC-anti-Human IgG and PE-gp120 tetramer. FIG. 3K shows counts of IgG+ and gp120+ spots. This result also shows that viable rare antigen-specific B cells could be rapidly and inexpensively isolated using this technique.

Figure 4A:
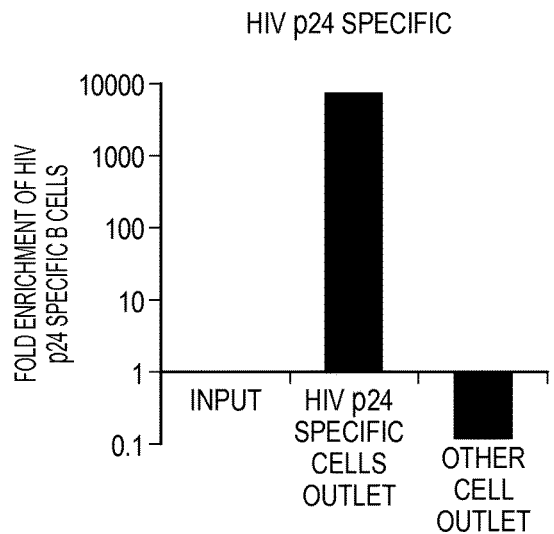
FIGS. 4A-4C are bar graphs showing isolation of rare antigen-specific cells from PBMC, as results of an experiment in accordance with an embodiment of the invention.
Figure 4B:
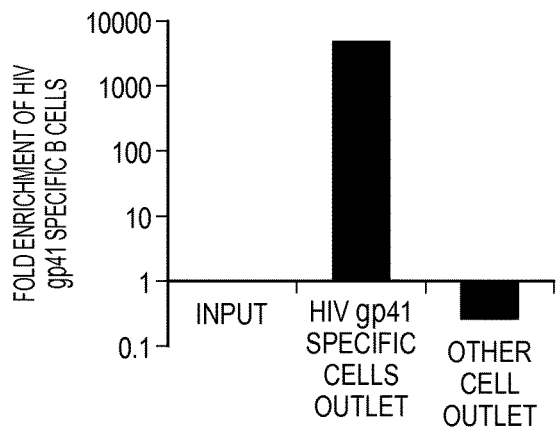
Figure 4C:
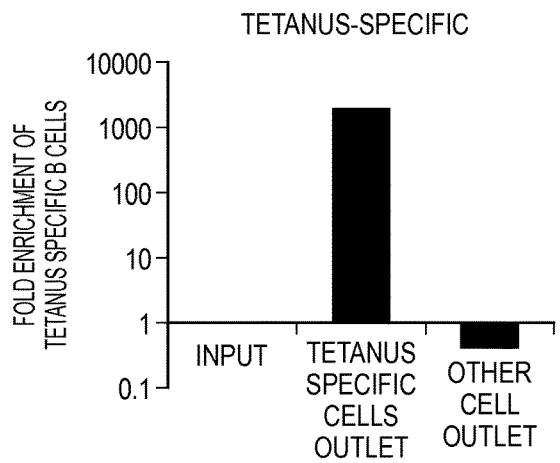

FIGS. 4A-4C are bar graphs showing isolation of rare antigen-specific cells from PBMC, as results of an experiment in accordance with an embodiment of the invention. FIGS. 4A and 4B show the isolation of HIV p24-specific cells and gp41-specific cells (<1 in 10,000), respectively, from PBMC from HIV patients. FIG. 4C shows the isolation of tetanus-specific cells (<1 in 100,000) from PBMC from a healthy donor.

Figure 5A:
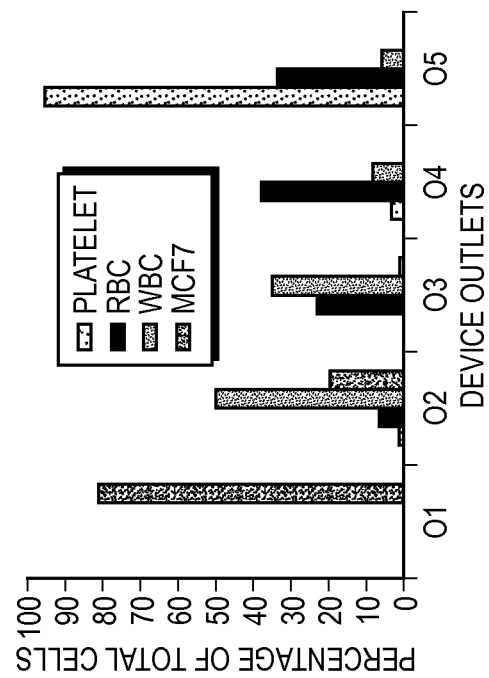
FIGS. 5A and 5B are bar graphs showing results of an experiment in accordance with an embodiment of the invention, in which there was performed the isolation of CD4+ cells (FIG. 5A) and spiked-in breast cancer (MCF7) cells (FIG. 5B) directly from whole blood.
Figure 5B:
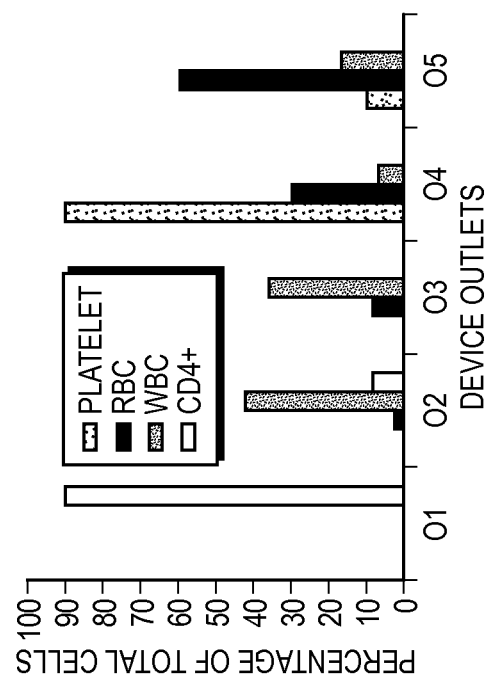

Further, affinity isolation of specific cells, directly from whole blood was demonstrated using the same device. FIGS. 5A and 5B are bar graphs showing results of an experiment in accordance with an embodiment of the invention, in which there was performed the isolation of CD4+ cells (FIG. 5A) and spiked-in breast cancer (MCF7) cells (FIG. 5B) directly from whole blood. Focusing of blood components—white blood cells (WBC), red blood cells (RBC) and platelets in different outlets is also observed. Flow rates were optimized to focus blood cells (red blood cells, white blood cells, platelets) and it was observed that red blood cells, white blood cells and platelets were focused to different outlets based on their different sizes. Staining of whole blood with PE-labeled anti-CD4 antibody and subsequent incubation with 15 μm beads coated with an anti-PE antibody, enabled the isolation of CD4+ cells directly from whole blood (FIG. 5A). Also breast cancer cells (MCF-7) spiked in at low concentrations (1000 cells/ml whole blood) could be captured and isolated, based on their expression of the epithelial cell marker EpCAM, in a single step (FIG. 5B). This can be compared with the multistep isolation methods reported earlier (4).

REFERENCES (1) Kodituwakku, A. P., Jessup, C., Zola, H. & Roberton, D. M. Isolation of antigen-specific B cells. *Immunol Cell Biol* 81, 163-170 (2003).
(2) Pape, K. A., Taylor, J. J., Maul, R. W., Gearhart, P. J. & Jenkins, M. K. Different B cell populations mediate early and late memory during an endogenous immune response. *Science* 331, 1203-1207, doi:10.1126/science. 1201730 (2011).
(3) Bhagat, A. A. S., Kuntaegowdanahalli, S. S. & Papautsky, I. Continuous particle separation in spiral microchannels using Dean flow based differential migration. *Lab Chip* 8, 1906-1914 (2008).
(4) Hou, H. W. et al. Isolation and retrieval of circulating tumor cells using centrifugal forces. *Sci. Rep.* 3, doi: www.nature.com/srep/2013/130212/srep01259/abs/srep01259.html-supplementary-information (2013).
(5) Ozkumur, E. et al. Inertial Focusing for Tumor Antigen-Dependent and Independent Sorting of Rare Circulating Tumor Cells, *Sci Trans Med* 5, 179, p179ra47 (2013).
(6) H. W. Hou, M. E. Warkiani, B. L. Khoo, Z. R. Li, R. A. Soo, D. S.-W. Tan, W.-T. Lim, J. Han, A. A. S. Bhagat and C. T. Lim, Sci. Rep., 2013, 3, 1259.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of separating at least one of a protein and a cell from a biological mixture, the method comprising:
   flowing a plurality of types of at least one of proteins and cells through at least one inlet of a spiral microfluidic device, each different type of the at least one of proteins and cells being bound to a corresponding different size of bead, the binding being based on an affinity between each such type of the at least one of proteins and cells and at least a portion of a surface of a bead to which each such type is bound;
   flowing the plurality of types of the at least one of proteins and cells, bound to the corresponding different sizes of beads, from the at least one inlet through a spiral channel of the spiral microfluidic device, thereby sorting, along a cross-section of the spiral channel, the plurality of types of the at least one of proteins and cells based on effective sizes of a plurality of combination particles, each combination particle comprising a type of the at least one of the protein and the cell bound to the corresponding different size of bead to which each type of the at least one of the protein and the cell is bound; and
   flowing the sorted types of the at least one of proteins and cells through a plurality of outlets of the spiral microfluidic device that are in fluid flow connection with the spiral channel, such that each outlet flows substantially only one type of the at least one of proteins and cells, bound to the corresponding different size of bead to which each such type is bound.

2. The method of claim 1, wherein the at least one of the protein and the cell comprises an antigen-specific antibody.

3. The method of claim 1, wherein the at least one of the protein and the cell comprises an antigen-specific cell.

4. The method of claim 1, wherein the at least one of the protein and the cell comprises a circulating tumor cell.

5. The method of claim 1, wherein the biological mixture comprises at least one blood component.

6. The method of claim 1, wherein the biological mixture comprises whole blood.

7. The method of claim 1, wherein the biological mixture comprises serum.

8. The method of claim 7, wherein the biological mixture comprises a polyclonal serum.

9. The method of claim 1, wherein each size bead of the corresponding different sizes of beads comprises a coated surface comprising a different type of at least one of an antigen or antibody that comprises an affinity with the corresponding at least one of the protein and the cell.

10. The method of claim 1, wherein the plurality of types of at least one of proteins and cells comprises more than two types of at least one of proteins and cells.

11. The method of claim 1, wherein the spiral channel has a length, and the cross-section has a height and a width defining an aspect ratio, such that the spiral channel is adapted, by virtue of the length and the cross-section, to sort, along a cross-section of the spiral channel, the plurality of types of the at least one of proteins and cells based on the effective sizes of the plurality of combination particles.

\* \* \* \* \*